United States Patent
Siewerdsen et al.

(10) Patent No.: US 10,368,956 B2
(45) Date of Patent: Aug. 6, 2019

(54) MR-LEVELCHECK-2: METHOD FOR LOCALIZATION OF STRUCTURES IN PROJECTION IMAGES

(71) Applicant: THE JOHNS HOPKINS UNIVERSITY, Baltimore, MD (US)

(72) Inventors: Jeffrey H. Siewerdsen, Baltimore, MD (US); Wathudurage Tharindu De Silva, Baltimore, MD (US); Ali Uneri, Baltimore, MD (US); Michael Ketcha, Baltimore, MD (US); Sureerat Reaungamornrat, Baltimore, MD (US); Jean-Paul Wolinsky, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/434,123

(22) Filed: Feb. 16, 2017

(65) Prior Publication Data

US 2017/0231713 A1    Aug. 17, 2017

Related U.S. Application Data

(60) Provisional application No. 62/295,653, filed on Feb. 16, 2016.

(51) Int. Cl.
*A61B 34/10* (2016.01)
*A61B 5/00* (2006.01)
(Continued)

(52) U.S. Cl.
CPC .............. *A61B 90/36* (2016.02); *A61B 5/055* (2013.01); *A61B 5/4566* (2013.01); *A61B 34/10* (2016.02);
(Continued)

(58) Field of Classification Search
None
See application file for complete search history.

(56) References Cited

U.S. PATENT DOCUMENTS

| | | | |
|---|---|---|---|
| 2007/0066887 A1* | 3/2007 | Mire | A61B 90/39 600/424 |
| 2012/0143090 A1* | 6/2012 | Hay | A61B 6/505 600/587 |

(Continued)

OTHER PUBLICATIONS

Uneri et al., "3D-2D registration for surgical guidance: effect of projection view angles on registration accuracy," Phys. Med. Biol. 59 (2014) 271-287.*

(Continued)

*Primary Examiner* — Soo Shin
(74) *Attorney, Agent, or Firm* — Harrity & Harrity, LLP

(57) ABSTRACT

An embodiment in accordance with the present invention provides a technique for localizing structures of interest in projection images (e.g., x-ray projection radiographs or fluoroscopy) based on structures defined in a preoperative 3D image (e.g., MR or CT). Applications include, but are not limited to, spinal interventions. The present invention achieves 3D-2D image registration (and particularly allowing use with a preoperative MR image) by segmenting the structures of interest in the preoperative 3D image and generating a simulated projection of the segmented structures to be aligned with the 2D projection image. Other applications include various clinical scenarios involving 3D-2D image registration, such as image-guided cranial neurosurgery, orthopedic surgery, biopsy, and radiation therapy.

22 Claims, 4 Drawing Sheets

(51) Int. Cl.
A61B 5/055 (2006.01)
A61B 90/00 (2016.01)
G01R 33/56 (2006.01)
G06T 7/00 (2017.01)
G06T 7/11 (2017.01)

(52) U.S. Cl.
CPC .... *G01R 33/5608* (2013.01); *A61B 2034/105* (2016.02); *A61B 2034/107* (2016.02); *A61B 2090/367* (2016.02); *A61B 2090/374* (2016.02); *A61B 2576/02* (2013.01); *G06T 7/0012* (2013.01); *G06T 7/11* (2017.01); *G06T 2207/10004* (2013.01)

(56) References Cited

U.S. PATENT DOCUMENTS

| | | | | |
|---|---|---|---|---|
| 2012/0271151 | A1* | 10/2012 | LaVoilette | A61B 5/06 600/411 |
| 2015/0043798 | A1* | 2/2015 | Carrell | G06T 7/0012 382/131 |
| 2017/0020630 | A1* | 1/2017 | Johnson | A61B 90/96 |

OTHER PUBLICATIONS

Berger et al., "Marker-free motion correction in weight-bearing cone-beam CT of the knee joint," Med. Phys. 43 (3), Feb. 10, 2016.*

Otake, et al., Automatic localization of vertebral levels in x-ray fluoroscopy using 3D-2D registration: A tool to reduce wrong-site surgery. Physics in Medicine and Biology 2012, 57, 5485.

Otake, et al., 3D-2D registration in mobile radiographs: algorithm development and preliminary clinical evaluation. Physics in Medicine and Biology 2015, 60, 2075-2090.

Lo, et al., Automatic localization of target vertebrae in spine surgery: clinical evaluation of the LevelCheck registration algorithm. Spine 2015, 40, 476-483.

Schmid, et al., Segmentation of X-ray Images by 3D-2D Registration Based on Multibody Physics. Computer Vision—ACCV 2014, 675-687.

Varnavas, et al., Increasing the Automation of a 2D-3D Registration System. IEEE Transactions on Medical Imaging 2013, 32, 387-399.

Varnavas, et al., Fully Automated 2D-3D Registration and Vertification. Medical Image Analysis 2015, 26, 108-119.

Ketcha, et al., Automatic masking for robust 3D-2D image registration in image-guided spine surgery. Medical Imaging 2016, 9786.

De Silva, et al., 3D-2D image registration for target localization in spine surgery: investigation of similarity metrics providing robustness to content mismatch. Physics in Medicine and Biology 2016, 61, 3009-3025.

De Silva, et al., "LevelCheck" Localization of Spinal Vertebrae in Intraoperative Radiographs from Preoperative MRI. CARS 2016.

Heinrich, et al., MIND: Modality independent neighbourhood descriptor for multi-modal deformable registration. Medical Image Analysis 2012, 16, 1423-1435.

Yuan, et al., A continuous max-flow approach to Potts Model. Lecture Notes in Computer Science 2010, 6316, 379-392.

Klinder, et al., Automated model-based vertebra detection, identification, and segmentation in CT images. Medical Image Analysis 2009, 13, 471-482.

Neubert, et al., Automated detection, 3D segmentation and analysis of high resolution spine MR images using statistical shape models. Physics in Medicine and Biology 2012, 57, 8357-8376.

* cited by examiner

Radiograph with labels | Projection from MR image | GO metric (u,v)

12
MR-LEVELCHECK-2: METHOD FOR LOCALIZATION OF STRUCTURES IN PROJECTION IMAGES

CROSS REFERENCE TO RELATED APPLICATIONS

This application claims the benefit of U.S. Provisional Patent Application No. 62/295,653 filed Feb. 16, 2016, which is incorporated by reference herein, in its entirety.

GOVERNMENT LICENSE RIGHTS

This invention was made with government support under NIH R01 EB017226 awarded by the National Institutes of Health (NIH). The government has certain rights in the invention.

FIELD OF THE INVENTION

The present invention relates generally to imaging. More particularly the present invention relates to a method for localization of structures in projection images.

BACKGROUND OF THE INVENTION

Intraoperative images such as radiographs and ultrasound are acquired during image-guided clinical interventions for localization, guidance, and verification of the operation. Target localization using human interpretation of intraoperative images can be a stressful, challenging task to the clinician, exacerbated by the time-sensitive constraints during clinical workflow. In such scenarios, solutions for intraoperative decision support could be valuable tools in assisting clinicians with the potential for improving clinical outcomes in image-guided clinical interventions and minimizing human error.

Preoperative images such as CT, MRI, PET, SPECT are acquired for diagnostic and planning purposes. These images are often superior in image quality and provide better 3D anatomical context to the clinician. Mapping information contained in preoperative imaging into the space of intraoperative images in real-time during procedure is a commonly used technique to convey clinically relevant information to assist the clinician. Since most intraoperative imaging modalities are available in 2D, such methods often require accurate and robust 3D-2D registration methods.

Preoperative and intraoperative imaging often contain complimentary details of anatomy. When multiple modalities are involved, such as preoperative MR images and intraoperative radiographs, there are usually drastic mismatches in image intensities/anatomical details caused primarily due to the differences in underlying imaging physics. Under such circumstances, mismatching content can drive 3D-2D registration to locally optimal solutions making it challenging to achieve accurate and robust performance.

It would therefore be advantageous to provide a 3D-2D registration method based on the segmentation of relevant anatomical regions in the 3D preoperative image. Recent advancements in image segmentation methods enable "intelligent" selection of gradients fulfilling a certain predefined objective criterion. Such capability allows to automatically extract relevant anatomical gradients from preoperative images and feed them into the registration. This approach aims to eliminate unnecessary, extraneous details contained in the preoperative image from the 3D-2D registration pipeline.

SUMMARY OF THE INVENTION

The foregoing needs are met, to a great extent, by the present invention, wherein in one aspect a method of performing a 3D to 2D registration of 3D image data to 2D image data where 3D image data is acquired in the form of a preoperative 3D magnetic resonance image of the subject. The method includes segmenting structures of interest in the preoperative 3D magnetic resonance image of the subject. The method also includes generating a simulated projection of the segmented structures to be aligned with the 2D image data and displaying a visual representation of the 3D image data registered onto the 2D image.

In accordance with an aspect of the present invention, the method includes programming the method on a non-transitory computer readable medium. The method includes registering 3D to 2D image data for the spine. The method includes segmenting the 3D image data with the objective function:

$$\min_{u(x)\in[0,1]} \langle 1-u, D^1 \rangle + \langle u, D^2 \rangle + \int g(x)|\nabla u(x)|dx.$$

The method can also include segmenting the 3D magnetic resonance image data with at least one chosen from: projecting MRI intensities (T2-weighted signal values) within each segmented vertebrae; dilating the segmentation to include a region approximating the bony cortex; projecting a binary region (disregarding image features internal to the segmentation); and projecting a vertebral body dilated to include the bone cortex. The method also includes registration of annotations defined in the 3D image (e.g., vertebral labels) with the 2D radiographic image—thereby extending the capability of previous work to allow 3D-2D registration and labeling based on a preoperative MRI.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
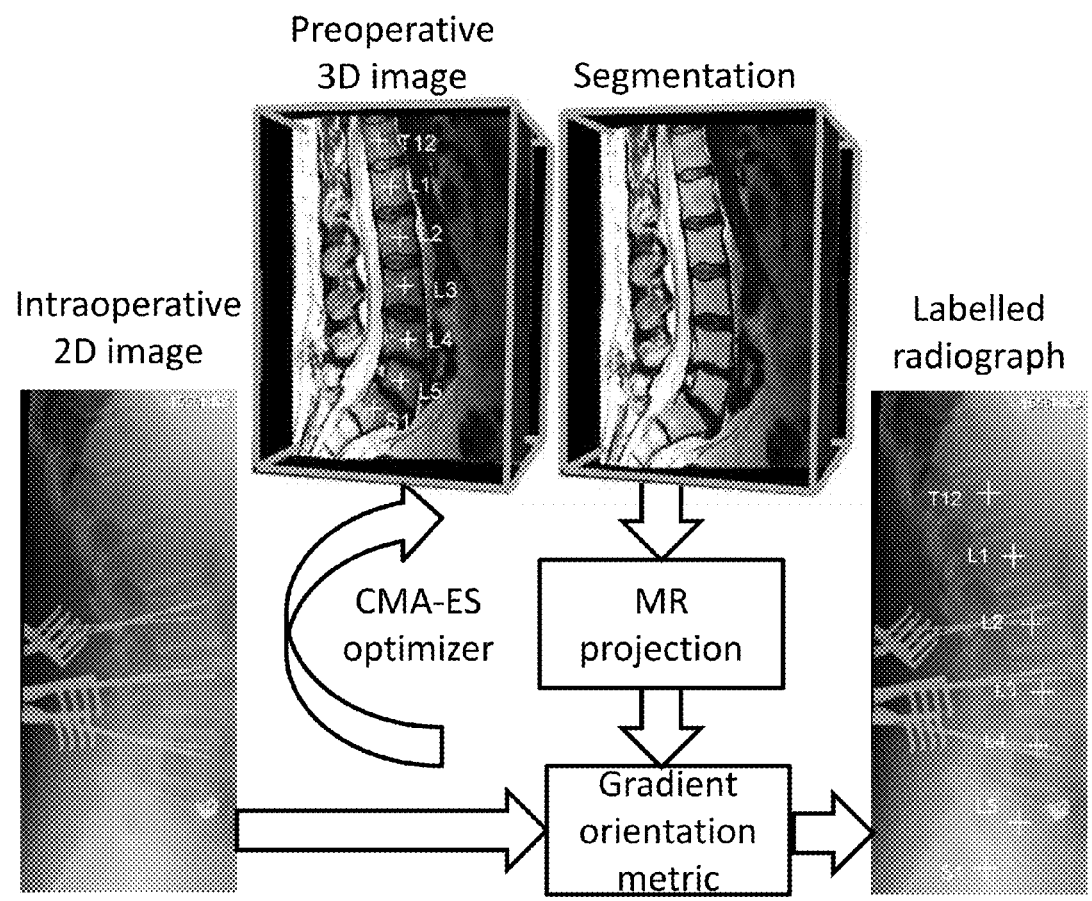
FIG. 1 illustrates a schematic view of a segmentation-based 3D-2D registration workflow using a gradient orientation similarity metric and a CMA-ES optimizer, as applied to a 3D-2D registration of the spine.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. In particular, the method of the present invention extends the functionality of ALL previously reported variations of the LevelCheck method (including 9 DoF, deformable, etc.) to the important case of a 3D MRI (instead of CT). This is important, since many times a preoperative MRI is preferred by the clinician.

An embodiment in accordance with the present invention provides a technique for localizing structures of interest in projection images (e.g., x-ray projection radiographs or fluoroscopy) based on structures defined in a preoperative 3D image (e.g., MR or CT). Applications include, but are not limited to, spinal interventions. The approach is analogous to a previous method (the "LevelCheck" algorithm) in which a preoperative 3D image (viz., CT) is registered to a 2D projection image, and labels defined in the 3D image can thereby be overlaid on the 2D image (e.g., labels of spinal vertebrae). LevelCheck leverages high-speed computing to provide surgeons with an on-demand, labeled visual depiction of the spine and surgical target in image acquired in the operating room. LevelCheck uses high-speed GPU computing to quickly register a patient's preoperative 3D CT scan to 2D x-ray images obtained in the operating room. The registration allows any information defined in the 3D preoperative image to be accurately overlaid on the intraoperative image. In labeling vertebrae, for example, LevelCheck provides decision support and assistance beyond manual level counting to help ensure that the surgeon is targeting the correct vertebral level.

Note that the previous method is well suited to preoperative CT but is not appropriate to preoperative MR due to fundamental mismatch/non-correspondence of anatomical features (e.g., signal intensities and image gradients) in MR and x-ray imaging technologies. The technique described below (nominally referred to as MR-LevelCheck-2) achieves 3D-2D image registration (and particularly allowing use with a preoperative MR image) by segmenting the structures of interest in the preoperative 3D image and generating a simulated projection of the segmented structures to be aligned with the 2D projection image. The approach is robust to the large mismatch between anatomical features in different modalities (e.g., MR and radiography) but maintains other advantageous aspects of the previous (LevelCheck) algorithm. A major aspect of significance of the current invention is the extension of LevelCheck capability to scenarios where only a preoperative MR is available (and not preoperative CT). Specific implementation is described for spine level localization that can be fully automated and does not require additional workflow from current standards of care in spine surgery. Other applications include various clinical scenarios involving 3D-2D image registration, such as image-guided cranial neurosurgery, orthopedic surgery, and radiation therapy.

The method of the present invention uses anatomical structures-of-interest that are segmented in preoperative 3D images to overcome strong image mismatch between modalities. For example, whereas previous implementations were limited to preoperative CT or "synthesized" a synthetic CT from an MR image. The present invention allows registration based on preoperative MR (or other preoperative 3D imaging modalities) without synthesis.

Specifically, the method performs forward projection on the 3D segmented structures rather than the 3D image itself, thereby overcoming strong mismatch in image intensities and gradients that present between different imaging modalities. The method has identified specific forms of forward projection of the segmented structures that is well suited to registration of preoperative MR with an intraoperative radiograph.

Specific implementations of the present invention can automatically segment the structures of interest using features (viz., vertebral labels) that are already defined (either manually or automatically) in preoperative planning and therefore does not require any additional workflow steps requiring manual input. The present invention can also use existing image protocols (e.g., sagittal T2-weighted MR images of the spine), without acquisition of any additional images or alternative MR scan sequences, thereby saving time, cost, and resources.

Previous work provides a method for 3D-2D registration based on preoperative CT with specific implementation in spine level localization. The current work extends functionality to work with preoperative MR images. Previous work accomplishes 3D-2D registration using preoperative MR by performing a "CT synthesis" step, essentially deriving a CT-like image from the MR image. That method is shown to work best for specific MR image sequences (viz., the UTE acquisition sequence, which may or may not be commonly acquired in the standard of care) and may not be generally applicable to other sequences. The current invention works with any pulse sequence in which structures of interest may be segmented (e.g., T2-weighted images that are commonly acquired as preoperative images for spine surgery).

3D MR image data is obtained either through a MR scan of the subject or use of previous MR scans of the subject. The MR image data is segmented before registration begins. This segmentation can be done in conjunction with the method of the present invention. Alternately, segmented image data can be segmented previously in conjunction with the MR scan. Pre-defined planning information (e.g., targets delineated in the 3D image) can be utilized to initialize the segmentation algorithm without requiring any additional manual input. The segmentation extracts relevant anatomy in the 3D image to be aligned with the 2D x-ray image and avoids undesirable solutions from the registration search space. This is a very helpful feature in multi-modal registration problems with many locally optimal solutions. In the present invention, 3D-2D registration is performed following a segmentation step of the 3D image. A non-transitory computer readable medium is programmed for executing the registration of the 3D image to the 2D image. This process is MR specific, as CT 3D to 2D registration was not operable with the 3D MR image data. The method of the present invention resolves fundamental mismatch/non-correspondence of anatomical features (e.g., signal intensities and image gradients) in MR and x-ray imaging technologies through programming of the non-transitory computer readable medium. After the 3D image data is registered to the 2D x-ray image, the resultant knitted 3D-2D registered image is displayed to the physician and surgical team. The 3D-2D image preferably also includes labels on the image to denote landmarks and anatomical structures for the surgical intervention. These labels can be added to the image via a GUI or can be imported from labels on the MR or x-ray image data.

Note that in the specific embodiment described below, in application to spine labeling, the segmentation can be accomplished automatically. This is because spine labels are defined in the 3D image as part of standard workflow and planning. Such spine labels can be as simple as single points defined in the 3D image (e.g., a point defined at the centroid of each vertebral body labeling that level of the spine). That point can be used to "seed" the segmentation process by region growing or other existing segmentation methods to reliably segment the vertebral body about each "seed" point. An example form of segmentation is shown below that reliably and automatically segments each vertebral body based on the definition a single point within each vertebrae. The registration process is shown to work better, if each segmented vertebral body is slightly expanded ("dilated") to include an additional surrounding layer approximating the bone cortex. The bony cortex appear as a dark layer in the MR image and therefore not captured in the segmentation output.

Alternative embodiments include developing advanced image similarity metrics that could handle multi-modality registration. However, the success of such methods is subject to the degree of mismatch encountered between the two images. When it involves multiple modalities of imaging with different underlying imaging physics, the structures could appear very differently confounding even advanced similarity metrics. Another alternative embodiment would be to develop robust optimization methods to overcome local optima. But current state-of-the-art optimization techniques suffer from locally optimal solutions under the time constraints of the applications. In the proposed invention, the problem is simplified by eliminating extraneous details. Therefore, desirable performance is achievable with currently available similarity metrics and optimization methods.

Another can include acquiring intermediate image modalities to simplify the problem. In such an approach, the content mismatch between the two modalities could be mitigated by using this intermediary image. However, such solutions require additional cost, time, and resources to the clinical workflow, whereas the solution of the present invention has the advantage of operating within existing clinical protocols.

According to an embodiment of the present invention, a segmentation is performed as an initial step during registration workflow. The annotations delineated by the clinician for planning purposes can be used as input to extract relevant anatomical structures. Using such annotations ($c_i$) as initialization, the present invention includes an automatic segmentation algorithm that can detect structures of interest from a preoperative 3D image that could be subsequently used in registration. Image segmentation was formulated as a spatially continuous min-cut problem with the objective function:

$$\min_{u(x) \in \{0,1\}} \langle 1 - u, D^1 \rangle + \langle u, D^2 \rangle + \int g(x) |\nabla u(x)| dx$$

where $u(x) \in \{0,1\}$ is an indicator function determining whether each pixel lies inside ($u(x)=1$) or outside ($u(x)=0$) the segmentation. $D^1$ and $D^2$ are data-fidelity terms that were defined using the image intensity difference between the pixel I and the mean intensity $I_{c_i}$ of a neighborhood proximal to the nearest annotation ($c_i$) as $D^1 = |I - \overline{I_{c_i}}|$ and using the gradient-weighted distance from the nearest annotation as $D^2 = \int_{c_i}^x \nabla I\, dx$. Smoothness term was defined as $$g(x) = \lambda \left( 1 + \exp\left(-\frac{1}{\nabla I}\right) \right)$$

where $\lambda$ is a regularization parameter. This objective function can be solved globally and exactly to obtain the segmentation output.

3D-2D registration involves projection of the 3D image iteratively aligned with the intraoperative 2D image and optimization according to an image similarity measure. In the present invention, the method is to project based on the segmentation of the 3D image, highlighting only the relevant anatomical structures that need to be aligned during registration. In each case, 3D-2D rigid registration can then be performed as illustrated in FIG. 1 using gradient orientation (GO) as a similarity metric and the covariance-matrix-adaptation-evolutionary-strategy (CMA-ES) optimizer. More particularly, FIG. 1 illustrates a schematic view of a segmentation-based 3D-2D registration workflow using a gradient orientation similarity metric and a CMA-ES optimizer, as applied to a 3D-2D registration of the spine.

The following includes a description of an exemplary implementation of the present invention. This example is not meant to be considered limiting, and any implementation of the known to or conceivable to one of skill in the art. While the present invention is discussed with respect to spinal images, any anatomical structure could be treated in the same way. This exemplary embodiment applies to preoperative MRI, while maintaining desirable properties like robustness against anatomical deformation, image content mismatch (surgical devices present in the intraoperative image but not the preoperative), and large capture range (multi-start optimization). This enables decision support to increasingly common scenarios in which MRI (not CT) is used for preoperative visualization and planning. Direct extension of the original LevelCheck method to MRI typically leads to failure due to large mismatch in image intensity and tissue correspondence between MRI and radiographs, but the present invention overcomes such challenges using a simple segmentation of vertebrae. Therefore, a new method of registering 3D MR image data to 2D x-ray image data was necessary.

As with conventional LevelCheck, the nominal position (e.g., centroids) of vertebral labels are annotated manually (or perhaps automatically, in the preoperative MRI using standard designations (C1-S1). Providing these vertebral centroids ($c_i$) as input, image segmentation can be performed using the method described above. Data terms ($D^1$ and $D^2$) of the objective function are defined using the image intensity difference between the pixel I and the mean intensity $I_{c_i}$ of a neighborhood proximal to the nearest vertebrae centroid ($c_i$) as $D^1 = |I - \overline{I_{c_i}}|$ and using the gradient-weighted distance from the nearest vertebrae centroid as $D^2 = \int_{c_i}^x \nabla I\, dx$.

Figure 2:
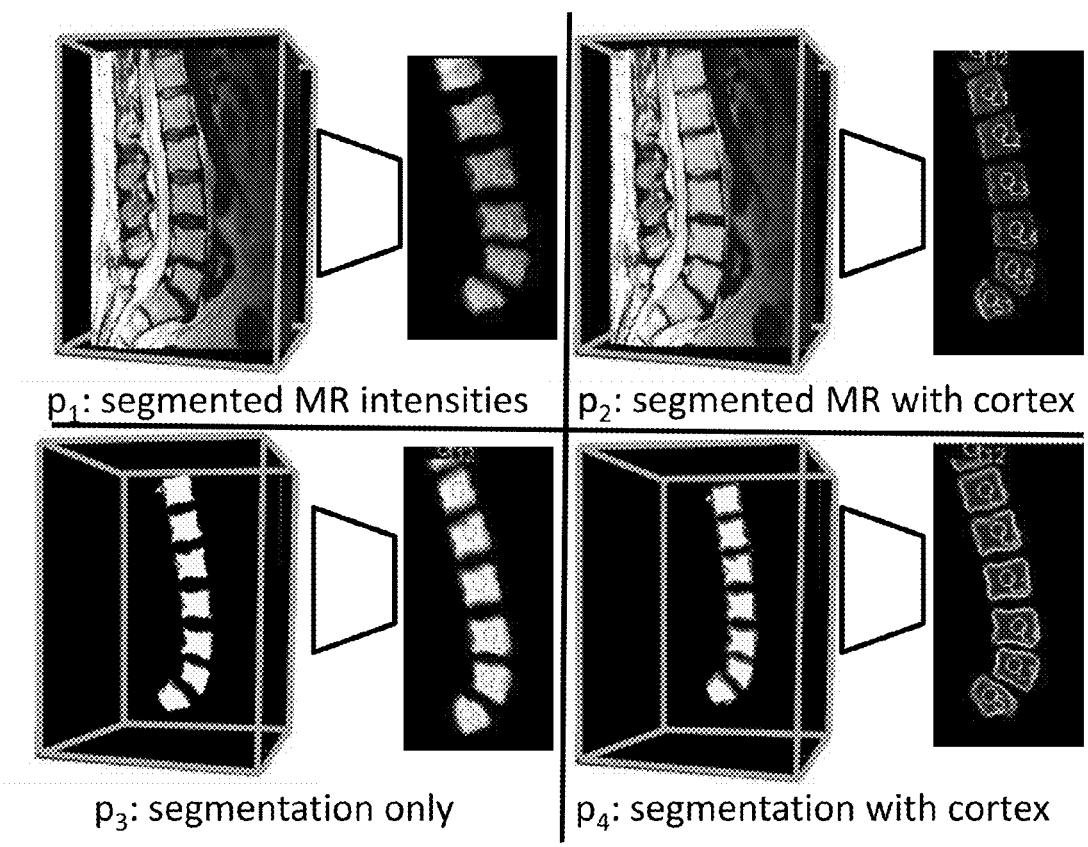
FIG. 2 illustrates an image comparison of four methods developed for image projection of the segmentation. The experiments indicated projecting the vertebral body with dilation to include bony cortex yielded the most robust performance.
Figure 3:
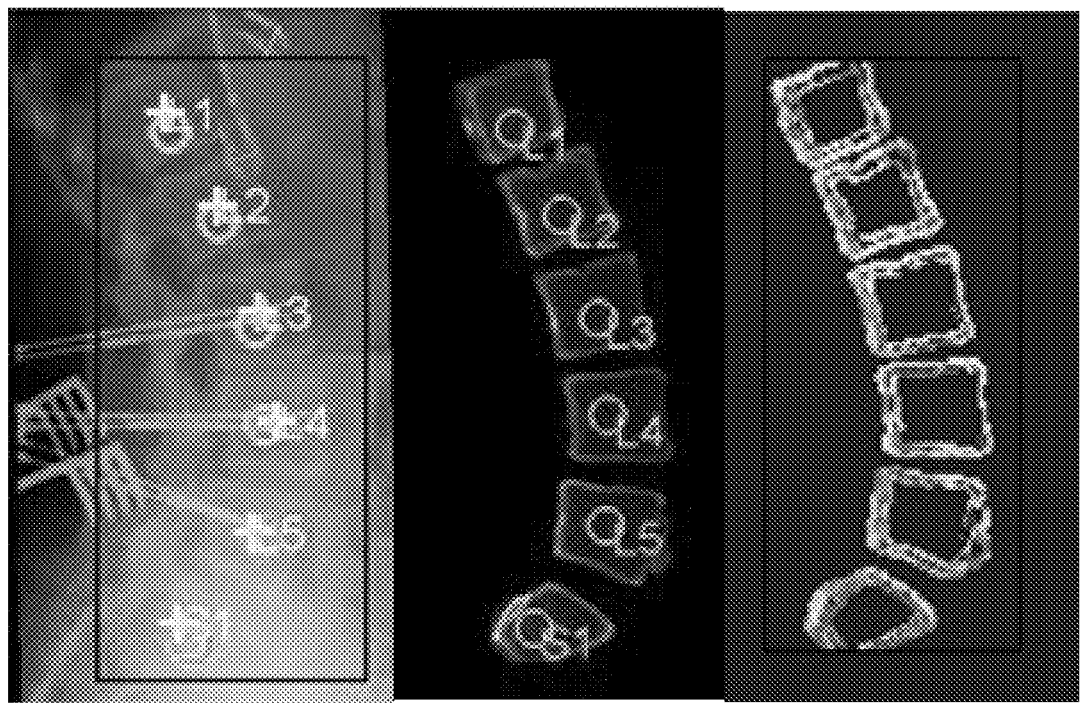
FIG. 3 illustrates an image view of an exemplary registration output for one patient from the clinical study.

During 3D-2D registration, projection of the MR image (or segmentation therein) is iteratively aligned with the intraoperative radiograph and optimization according to an image similarity measure. Due to strong differences in MRI and radiographic image intensities, tissue correspondence, etc., obtaining a radiograph-like image from MRI projections is not straightforward. Using the segmentation result, however, four approaches to generate MR projections are shown in FIG. 2: the p1 method projects the original MRI intensities (T2-weighted signal values) within each segmented vertebrae; the p2 approach first dilated the segmentation to include a region approximating the bony cortex and then projected as in p1; the p3 method projected the p1 segmentation as a binary region (disregarding image features internal to the segmentation); and the p4 method projected the vertebral body as in p3 dilated to include the bone cortex. More particularly, FIG. 2 illustrates an image comparison of four methods investigated for image projection of the segmentation. The experiments indicated projecting the vertebral body with dilation to include bony cortex yielded the most robust performance. An example case for registration in a clinical study is shown in FIG. 3. FIG. 3 illustrates an image view of an exemplary registration output for one patient from the clinical study. Circles show localization, overlaid with ground truth (crosses).

The method leverages the same underlying framework for robust, high-speed 3D-2D registration and overcomes dissimilarities in image intensities, gradients, and tissue correspondence through a simple segmentation of vertebrae in MRI. The segmentation is seeded by the same 3D vertebral label, thus adding no additional workflow to the process. The method can also function using the imaging protocols adhered in standard-of-care sagittal MR images acquired for diagnosis and lateral radiographs acquired for intraoperative localization.

The work described herein extends 3D to 2D registration to a method based on preoperative MRI. The method maintains desirable properties of robustness against anatomical deformation, image content mismatch (surgical devices present in the intraoperative image but not the preoperative), and large capture range (multi-start optimization) while extending the approach to increasingly common scenarios in which MRI (not CT) is used for preoperative visualization and planning. Direct extension of the previous method is confounded by large mismatch in image intensity and tissue correspondence between MRI and radiographs, but the work reported herein overcomes such challenges using a simple segmentation of vertebrae.

In another exemplary implementation of the present invention, clinical image data were collected in a study involving 5 patients undergoing thorocolumbar spine surgery and receiving a preoperative MRI. There were no changes to standard-of-care imaging protocols for either the preoperative 3D images (sagittal T2-weighted MM) or intraoperative 2D images (lateral mobile radiographs).

As with conventional LevelCheck, the centroids of vertebral labels are annotated manually in the preoperative MRI using standard designations (C1-S1). Providing these vertebral centroids ($c_i$) as input, an automatic segmentation algorithm is used to extract vertebrae boundaries from the MRI to be subsequently used in registration. Image segmentation was formulated as a spatially continuous min-cut problem with the objective function:

$$\min_{u(x)\in[0,1]} \langle 1-u, D^1 \rangle + \langle u, D^2 \rangle + \int g(x)|\nabla u(x)|dx$$

where $(x) \in \{0,1\}$, is an indicator function determining whether each pixel lies inside ($u(x)=1$) or outside ($u(x)=0$) the vertebrae. Data terms ($D^1$ and $D^2$) were defined using the image intensity difference between the pixel I and the mean intensity $I_{c_i}$ of a neighborhood proximal to the nearest vertebrae centroid ($c_i$) as $D^1=|I-\overline{I_{c_i}}|$ and using the gradient-weighted distance from the nearest vertebrae centroid as $D^2=\int_{c_i}^x \nabla I\,dx$. The smoothness term was defined as $$g(x) = \lambda\left(1 + \exp\left(-\frac{1}{\nabla I}\right)\right)$$

where $\lambda$ is a regularization parameter. This objective function was solved globally to obtain the segmentation output.

3D-2D registration involves projection of the MR image (or segmentation therein) iteratively aligned with the intraoperative radiograph and optimization according to an image similarity measure. Due to strong differences in MRI and radiographic image intensities, tissue correspondence, etc., obtaining a radiograph-like image from MRI projections is not straightforward. Using the segmentation result, however, four approaches to generate MR projections can be used as shown in FIG. 2: the p1 method projects the original MRI intensities (T2-weighted signal values) within each segmented vertebrae; the p2 approach first dilated the segmentation to include a region approximating the bony cortex and then projected as in p1; the p3 method projected the p1 segmentation as a binary region (disregarding image features internal to the segmentation); and the p4 method projected the vertebral body as in p3 dilated to include the bone cortex. In each case, 3D-2D rigid registration was performed as in FIG. 1 using gradient orientation (GO) as a similarity metric and the covariance-matrix-adaptation-evolutionary-strategy (CMA-ES). Intrinsic and extrinsic parameters were empirically determined to generate a comparable projection from the MRI, and manual initialization along the longitudinal direction of the spine was selected to provide initial overlap between the two images within ~40-110 mm initial error. By perturbing this manual initialization within a range ±100 mm, 10 repeated registrations were performed for each image-pair.

The accuracy and robustness of the segmentation method was evaluated by comparing to manually annotated segmentations of vertebral bodies and computing the Dice coefficient, mean absolute distance (MAD), and maximum absolute distance (MAXD). Registration accuracy was evaluated with respect to the task of vertebrae localization in the radiograph: ground truth vertebral locations defined in the radiographs were compared with the 3D-2D registration output to calculate projection distance error (PDE). Failure was defined as PDE>30 mm (a distance for which the registered label may lie outside the vertebral body). Registration run-time was measured on a Windows 7 64-bit workstation with an Intel Xeon processor (2.13 GHz) and nVidia GeForce Titan Black GPU, 6 GB memory, 2880 cores.

Nominal values for regularization parameters in the segmentation algorithm were evaluated in a sensitivity analysis. With the nominal settings, the segmentation accuracy across 5 patients was: Dice coefficient=89.2±2.3 (mean±stdev); MAD=(1.5±0.3) mm; and MAXD=(5.6±0.7) mm. The Dice and MAD results are comparable to other MR spine segmentation methods. The larger MAXD is attributed to nominal regularization parameter that emphasized distinct identification of the vertebrae boundary with some occasional protrusions at the vertebrae pedicle.

Figure 4:
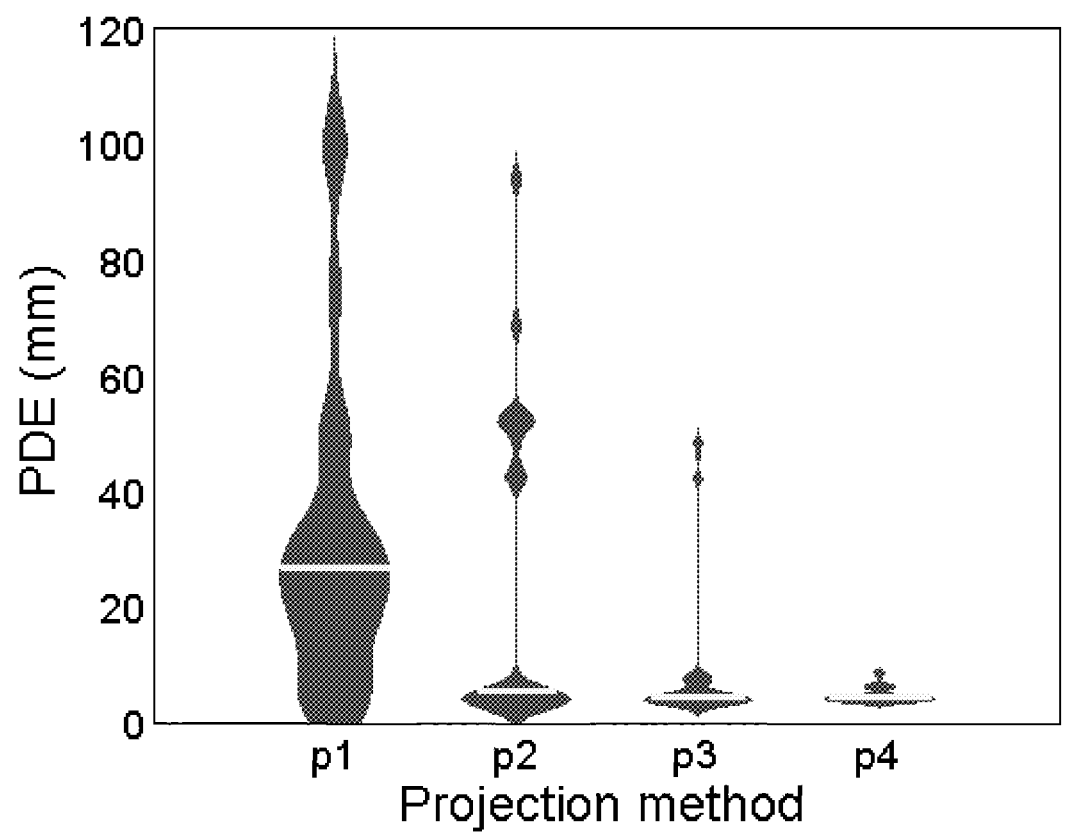
FIG. 4 illustrates a graphical view of violin plots showing distributions of projection distance error (PDE) for the four projection methods of FIG. 3.

Violin plots for the distributions in PDE for 5 patient registrations (each perturbed 10 times in initialization) are shown in FIG. 4. FIG. 4 illustrates a graphical view of violin plots showing PDE distributions for four projection methods. Performance is shown for the four projection methods: for the p1 method, PDE=(27.1±14.6) mm (median±iqr) with a 36% failure rate; the p2 method improved to PDE=5.9±46.7 mm but suffered in robustness and was also subject to 40% failure rate; the p3 method (projection of the binary segmentation) improved PDE to (4.9±3.2) mm with only 10% failure rate; and the p4 method (projection of the binary cortex) yielded the best performance, with PDE= (4.8±0.8) mm and all registrations converging at the desired solution.

The method of the present invention provides robust, high-speed 3D-2D registration and overcomes dissimilarities in image intensities, gradients, and tissue correspondence through a simple segmentation of vertebrae in MRI. The segmentation is seeded by 3D vertebral labels from the MR or x-ray, thus adding no additional workflow to the process. However, it may also be possible to allow a surgical team member to add additional labels after registration if desired. 3D-2D registration using the MRI segmentation dilated to include the bone cortex demonstrated registration performance with PDE<5 mm and 0% failure rate.

While the methods described in this invention were developed for robust 3D-2D registration between MR and radiographs of spine, their application, in principle, extend to other 3D-2D registration problems in multiple anatomical sites in different image-guided interventions. Its utility is especially beneficial to overcome large mismatches existing across pre- and intra-operative imaging which is usually the case in multi-modality imaging. Therefore this approach can be used in image-guided interventions in surgery, radiotherapy, or interventional radiology to assist the clinician in localization, guidance, and verification tasks with 3D-2D registration. This could also have general applicability outside the clinical domain, for various 3D-2D registration applications.

It should be noted that the methods of the present invention described above can be implemented with a computing device. The computing device can be hard wired to the imaging machine or can be networked in a wired or wireless manner. The computing device can also communicate with a server or other remote computing device in order to execute these steps. A non-transitory computer readable medium programmed to execute the methods can be loaded on the computing device or in communication with the computing device. The non-transitory computer readable medium can take any suitable form known to one of skill in the art. The non-transitory computer readable medium is understood to be any article of manufacture readable by a computer or other computing device. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art.

The program can also exist on a specially designed computer built with the specifications of the present invention in mind. The computing device is also configured to receive information from both a source of 3D image data and a source of 2D image data. The computing device should be configured for processing the registrations in real-time and also intraoperatively. Data can be transmitted from the imaging device or image database wirelessly, over a network, with storage media, or any other suitable means known to or conceivable to one of skill in the art. The computing device can also include a GUI such that users of the system can interact with the registered images produced as a result of the method of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method, comprising:
   receiving, by a device, 3D magnetic resonance image data in the form of a preoperative 3D magnetic resonance image of a subject;
   segmenting, by the device, structures of interest in the preoperative 3D magnetic resonance image of the subject,
   the structures of interest being segmented by using an automatic segmentation algorithm, and
   the structures of interest being segmented to mitigate non-correspondence of anatomical features between the 3D magnetic resonance image data and 2D image data,
   the 3D magnetic resonance image data and the 2D image data being acquired from different imaging modalities;
   generating, by the device, a simulated projection of the segmented structures of interest to be aligned with 2D image data of the subject;
   providing, by the device and for display, a visual representation of the structures of interest; and
   providing, by the device and for display, a visual representation of the 3D magnetic resonance image data registered onto the 2D image data of the subject.

2. The method of claim 1, further comprising:
   registering the 3D magnetic resonance image data onto the 2D image data of the subject for a spine.

3. The method of claim 1, further comprising:
   segmenting the 3D magnetic resonance image data with an objective function defined by:

$$\min_{u(x)\in[0,1]} \langle 1-u, D^1 \rangle + \langle u, D^2 \rangle + \int g(x)|\nabla u(x)|dx.$$

4. The method of claim 1, further comprising:
   segmenting the 3D magnetic resonance image data with one chosen from a group consisting of:
   projecting MRI intensities within each segmented vertebrae;
   dilating the segmentation to include a region approximating a bony cortex; and
   projecting a binary region and projecting a vertebral body dilated to include the bony cortex.

5. The method of claim 1, further comprising:
adding labels to the visual representation of the 3D magnetic resonance image registered onto the 2D image data.

6. The method of claim 1, further comprising:
applying annotations within the preoperative 3D magnetic resonance image of the subject to mark locations of the structures of interest.

7. The method of claim 6, further comprising:
initializing segmentation using the annotations applied within the preoperative 3D magnetic resonance image of the subject.

8. The method of claim 1, further comprising:
applying forward projection to the segmented structures of interest.

9. The method of claim 1, where mitigating the non-correspondence of the anatomical features comprises:
mitigating the non-correspondence of the anatomical features using one selected from a group consisting of:
signal intensities, and
image gradients.

10. The method of claim 4, wherein the MRI intensities are T2-weighted signal values.

11. A system, comprising:
one or more memories; and
one or more processors, communicatively coupled to the one or more memories, to:
receive 3D magnetic resonance image data in form of a preoperative 3D magnetic resonance image of a subject;
segment structures of interest in the preoperative 3D magnetic resonance image of the subject,
the structures of interest being segmented by using an automatic segmentation algorithm, and
the structures of interest being segmented to mitigate non-correspondence of anatomical features between the 3D magnetic resonance image data and 2D image data,
the 3D magnetic resonance image data and the 2D image data being acquired from different imaging modalities;
generate a simulated projection of the segmented structures to be aligned with 2D image data of the subject;
provide, for display, a visual representation of the structures of interest; and
provide, for display, a visual representation of the 3D magnetic resonance image data registered onto the 2D image data of the subject.

12. The system of claim 11, where the one or more processors are further to:
register 3D magnetic resonance image data to 2D image data for a spine.

13. The system of claim 11, where the one or more processors are to:
segment the 3D magnetic resonance image data with an objective function defined by:

$$\min_{u(x)\in[0,1]} \langle 1-u, D^1 \rangle + \langle u, D^2 \rangle + \int g(x)|\nabla u(x)|dx.$$

14. The system of claim 11, where the one or more processors are further to:
segment the 3D magnetic resonance image data with one chosen from a group consisting of:
projecting MRI intensities within each segmented vertebrae;
dilating the segmentation to include a region approximating a bony cortex;
projecting a binary region; and
projecting a vertebral body dilated to include the bony cortex.

15. The system of claim 11, where the one or more processors are further to:
add labels to the visual representation of the 3D magnetic resonance image registered onto the 2D image data of the subject.

16. The system of claim 11, where the one or more processors are further to:
apply annotations within the preoperative 3D magnetic resonance image to mark locations of the structures of interest.

17. The system of claim 16, where the one or more processors are further to:
initialize segmentation using the annotations applied within the preoperative 3D magnetic resonance image.

18. The system of claim 11, where the one or more processors are further to:
apply forward projection to the segmented structures of interest.

19. A method, comprising:
receiving, by a device, 3D magnetic resonance image data in the form of a preoperative 3D magnetic resonance image of a subject;
segmenting, by the device, structures of interest in the preoperative 3D magnetic resonance image of the subject;
segmenting, by the device, the 3D magnetic resonance image data with an objective function:

$$\min_{u(x)\in[0,1]} \langle 1-u, D^1 \rangle + \langle u, D^2 \rangle + \int g(x)|\nabla u(x)|dx;$$

generating, by the device, a simulated projection of the segmented structures of interest to be aligned with 2D image data of the subject;
providing, by the device and for display, a visual representation of the structures of interest; and
providing, by the device and for display, a visual representation of the 3D magnetic resonance image data registered onto the 2D image data of the subject.

20. The method of claim 19, further comprising:
adding labels to the visual representation of the 3D magnetic resonance image registered onto the 2D image data.

21. The method of claim 19, where
the structures of interest are segmented to mitigate non-correspondence of anatomical features between the 3D magnetic resonance image data and the 2D image data, and
the 3D magnetic resonance image data and the 2D image data are acquired from different imaging modalities.

22. A system, comprising:
one or more memories;
one or more processors, communicatively coupled to the one or more memories, to:
receive 3D magnetic resonance image data in the form of a preoperative 3D magnetic resonance image of a subject;

segment structures of interest in the preoperative 3D magnetic resonance image of the subject;
segment the 3D magnetic resonance image data with an objective function:

$$\min_{u(x)\in[0,1]} \langle 1-u, D^1 \rangle + \langle u, D^2 \rangle + \int g(x)|\nabla u(x)|dx;$$

generate a simulated projection of the segmented structures of interest to be aligned with 2D image data of the subject;
provide for display a visual representation of the structures of interest; and
provide for display a visual representation of the 3D magnetic resonance image data registered onto the 2D image data of the subject.

* * * * *